US009498110B2

(12) United States Patent
Asatori

(10) Patent No.: US 9,498,110 B2
(45) Date of Patent: Nov. 22, 2016

(54) ENDOSCOPE SYSTEM HAVING NARROW BAND OBSERVATION

(71) Applicant: OLYMPUS CORPORATION, Tokyo (JP)

(72) Inventor: Sachiko Asatori, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/824,555

(22) Filed: Aug. 12, 2015

(65) Prior Publication Data

US 2015/0342448 A1    Dec. 3, 2015

Related U.S. Application Data

(63) Continuation of application No. PCT/JP2014/063104, filed on May 16, 2014.

(30) Foreign Application Priority Data

May 29, 2013  (JP) ................................. 2013-113226

(51) Int. Cl.
  *A61B 1/045*    (2006.01)
  *A61B 1/06*    (2006.01)
  (Continued)

(52) U.S. Cl.
  CPC .............. *A61B 1/0638* (2013.01); *A61B 1/00* (2013.01); *A61B 1/0002* (2013.01);
  (Continued)

(58) Field of Classification Search
  CPC .............. A61B 1/0638; A61B 1/0646; A61B 1/00006; A61B 1/043; A61B 1/045; A61B 1/04; A61B 1/00009; H04N 5/2256; H04N 5/23245; H04N 5/232
  See application file for complete search history.

(56) References Cited

U.S. PATENT DOCUMENTS

| 5,233,416 A | 8/1993 | Inoue |
| 6,597,390 B1 * | 7/2003 | Higuchi ............... H04N 5/2256 348/65 |

(Continued)

FOREIGN PATENT DOCUMENTS

| EP | 1 908 393 A1 | 4/2008 |
| EP | 2604176 A1 | 6/2013 |

(Continued)

OTHER PUBLICATIONS

International Search Report dated Aug. 12, 2014 issued in PCT/JP2014/063104.

(Continued)

*Primary Examiner* — John P Leubecker
(74) *Attorney, Agent, or Firm* — Scully, Scott, Murphy & Presser, PC

(57) ABSTRACT

An endoscope system includes a light source unit that emits first and second narrow band light sequentially, a color filter in which first and second filters having different spectral characteristic are disposed, an image pickup device that receives light passing through the first filter in a first pixel and receives light passing through the second filter in a second pixel, and can set an exposing period and a reading period of an electric signal for each pixel, and a control unit that performs control for causing the first narrow band light to be emitted, causing the first pixels to be exposed, and reading an electric signal from the second pixel in a first period, and causing the second narrow band light to be emitted, causing the second pixel to be exposed, and reading an electric signal from the first pixel in a second period.

4 Claims, 2 Drawing Sheets

(51) Int. Cl.
*A61B 1/00* (2006.01)
*A61B 1/04* (2006.01)
*G02B 23/24* (2006.01)
*H04N 5/232* (2006.01)
*H04N 5/225* (2006.01)

(52) U.S. Cl.
CPC ............ *A61B 1/00006* (2013.01); *A61B 1/04* (2013.01); *A61B 1/045* (2013.01); *A61B 1/06* (2013.01); *A61B 1/0646* (2013.01); *A61B 1/0661* (2013.01); *G02B 23/2469* (2013.01); *H04N 5/2256* (2013.01); *H04N 5/232* (2013.01); *H04N 5/23245* (2013.01); *H04N 2005/2255* (2013.01)

(56) References Cited

U.S. PATENT DOCUMENTS

| | | | | |
|---|---|---|---|---|
| 2001/0009269 | A1* | 7/2001 | Hayashi | A61B 1/00009 |
| | | | | 250/458.1 |
| 2010/0094136 | A1* | 4/2010 | Nakaoka | A61B 1/043 |
| | | | | 600/477 |
| 2011/0063427 | A1* | 3/2011 | Fengler | A61B 1/00186 |
| | | | | 348/65 |
| 2013/0169843 | A1 | 7/2013 | Ono et al. | |
| 2014/0187881 | A1 | 7/2014 | Saito et al. | |
| 2014/0194686 | A1* | 7/2014 | Murayama | A61B 1/00009 |
| | | | | 600/109 |

FOREIGN PATENT DOCUMENTS

| | | |
|---|---|---|
| EP | 2754378 A1 | 7/2014 |
| JP | 2005-006974 A | 1/2005 |
| JP | 5259882 B2 | 8/2013 |
| WO | WO 2012/043771 A1 | 4/2012 |
| WO | WO 2013/035532 A1 | 3/2013 |

OTHER PUBLICATIONS

Extended Supplementary European Search Report dated Sep. 1, 2016 in related European Application No. 14 80 3469.7.

* cited by examiner

ENDOSCOPE SYSTEM HAVING NARROW BAND OBSERVATION

CROSS REFERENCE TO RELATED APPLICATION

This application is a continuation application of PCT/JP2014/063104 filed on May 16, 2014 and claims benefit of Japanese Application No. 2013-113226 filed in Japan on May 29, 2013, the entire contents of which are incorporated herein by this reference.

BACKGROUND OF THE INVENTION

1. Field of the Invention

The present invention relates to an endoscope system, and in particular, relates to an endoscope system that can perform narrow band light observation.

2. Description of the Related Art

In a medical field, for example, surgeries using apparatuses such as endoscopes that are minimally invasive to living bodies have been performed. In addition, as observation methods using endoscopes, observation methods such as normal light observation and narrow band light observation have been known, the normal light observation being an observation in which an object in a living body is irradiated with light beams having individual colors of R (red), G (green), and B (blue) to obtain an image having coloring substantially similar to that by observation with the naked eye, and the narrow band light observation being an observation in which an object in a living body is irradiated with light beams having narrower bands as compared with the illumination light beams of the normal light observation to obtain an image in which blood vessels and the like existing in mucosal epithelium of a living body are accentuated.

Then, for example, Japanese Patent Application Laid-Open Publication No. 2005-6974 discloses an endoscope apparatus that includes a configuration capable of being switched into respective modes corresponding to the above-described two kinds of observation.

In contrast, in many endoscope apparatuses including one disclosed in Japanese Patent Application Laid-Open Publication No. 2005-6974, either of a frame-sequential or simultaneous image pickup scheme is employed.

More specifically, the above-described frame-sequential image pickup scheme can be implemented as, for example, a configuration in which an image pickup device, including no color filter provided on an image pickup surface, picks up an image of return light generated by irradiating an object with frame-sequential light that is obtained by time-dividing illumination light having a plurality of wavelength band components.

In addition, the above-described simultaneous image pickup scheme can be implemented as, for example, a configuration in which an image pickup device picks up an image of return light generated by irradiating an object with illumination light having a plurality of wavelength band components, the image pickup device including a color filter, provided on an image pickup surface thereof, in which a plurality of minute filters each having a predetermined spectral characteristic are disposed in a predetermined pattern.

Individual filters that are included in a color filter provided on the image pickup surface of the image pickup device are typically configured to have a spectral characteristic of transmitting not only light having a predetermined color component but also light having a broad band from a visible range to a near-infrared range.

SUMMARY OF THE INVENTION

An endoscope system of an aspect of the present invention includes a light source unit that can emit first narrow band light and second narrow band light different from the first narrow band light sequentially; a color filter that is formed by disposing at least a first filter and a second filter, the first filter having a spectral characteristic that makes a transmittance in a band of a first color component including a band of the first narrow band light relatively higher than a transmittance in other bands, and the second filter having a spectral characteristic that makes a transmittance in a band of a second color component including a band of the second narrow band light relatively higher than a transmittance in other bands; an image pickup device that is configured to receive light passing through the first filter in a first pixel and receive light passing through the second filter in a second pixel different from the first pixel, and can set an exposing period and a reading period of an electric signal for each pixel; and a control unit that performs control for causing the first narrow band light to be emitted, causing the first pixel to be exposed, and reading an electric signal from the second pixel in a first period, and causing the second narrow band light to be emitted, causing the second pixel to be exposed, and reading an electric signal from the first pixel in a second period different from the first period.

DETAILED DESCRIPTION OF THE PREFERRED EMBODIMENTS

An embodiment of the present invention will be described below with reference to the drawings.

Figure 1:
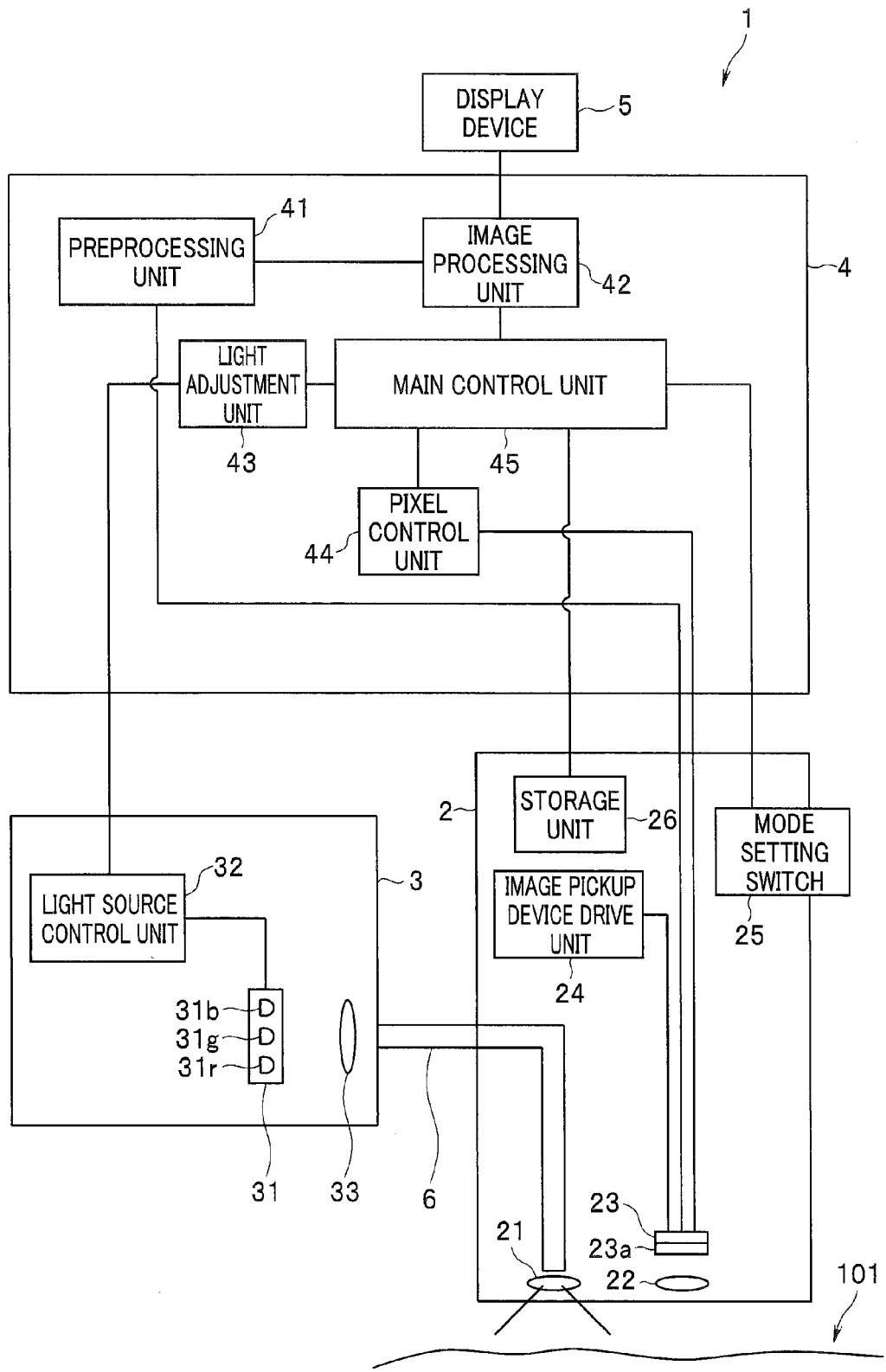
FIG. 1 is a diagram showing the configuration of the main part of an endoscope system in an embodiment.
Figure 2:
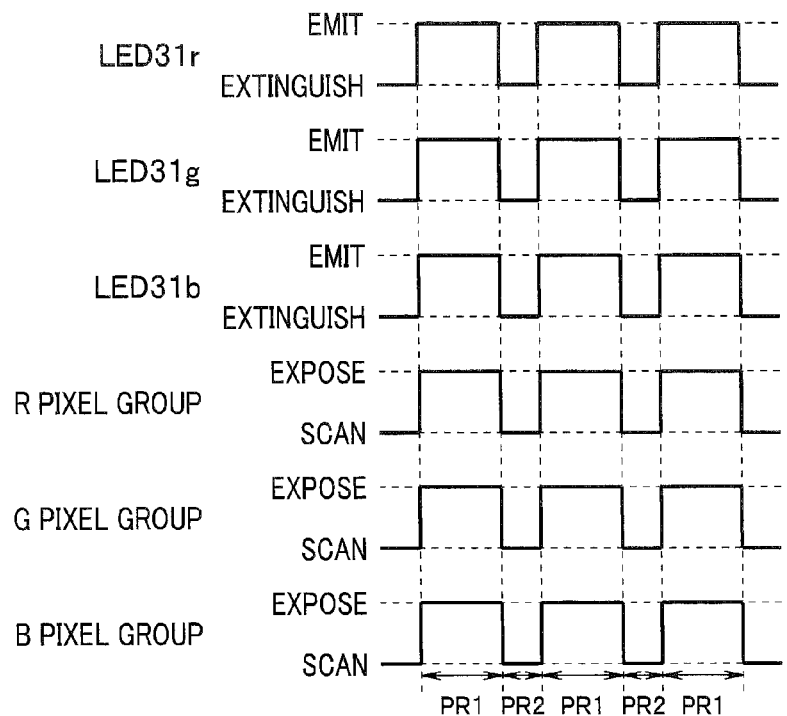
FIG. 2 is a diagram illustrating control performed when a normal light observation mode is set to the observation mode of the endoscope system in the embodiment.
Figure 3:
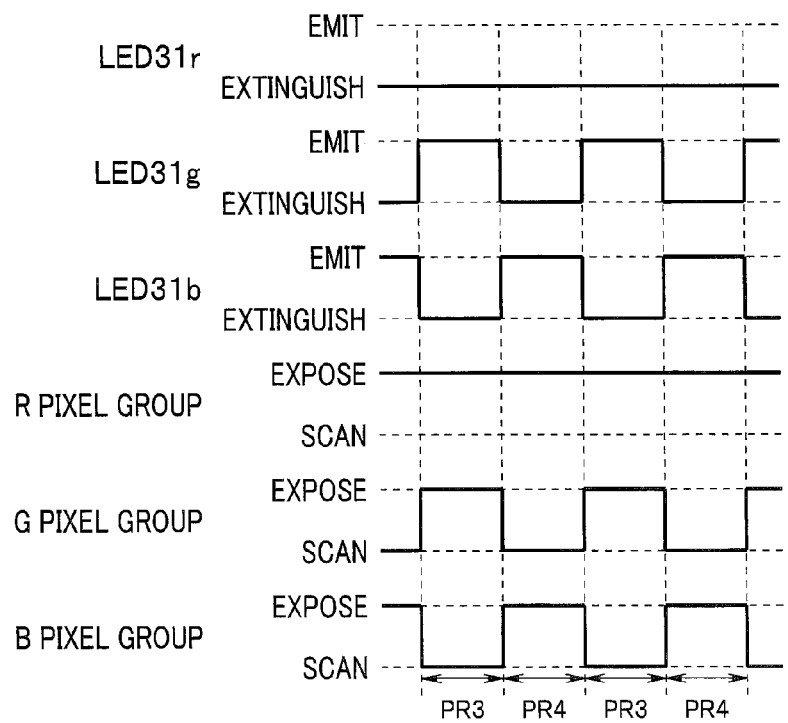
FIG. 3 is a diagram illustrating control performed when a narrow band light observation mode is set to the observation mode of the endoscope system in the embodiment.

FIG. 1 to FIG. 3 relate to the embodiment of the present invention. FIG. 1 is a diagram showing the configuration of the main part of an endoscope system in the embodiment.

An endoscope system 1 includes, as shown in FIG. 1, an endoscope 2 that has an elongated insertion portion that is insertable into a body cavity of a subject and is configured to pick up and acquire an image of an object 101 such as living tissue existing in the body cavity, a light source apparatus 3 that is configured to provide the endoscope 2 with illumination light with which the object 101 is irradiated, a processor 4 that is configured to generate and output a video signal corresponding to the image acquired by the endoscope 2, and a display device 5 that is configured to display the image corresponding to the video signals outputted from the processor 4. In addition, into the inside of the endoscope 2, a light guide 6 is inserted, the light guide 6 being configured to transmit the light provided by the light source apparatus 3 to the distal end portion of the endoscope 2.

The endoscope 2 has, in the distal end portion of the insertion portion, an illumination optical system 21 that irradiates the object 101 with the illumination light transmitted through the light guide 6, an objective optical system 22 that forms return light from the object 101 irradiated with the illumination light, an image pickup device 23 the image pickup surface of which is disposed at an image-forming position of the objective optical system 22, and a color filter 23a that is attached to the image pickup surface of the image pickup device 23.

In addition, the endoscope 2 has an image pickup device drive unit 24 that generates and outputs image pickup device drive signals used to drive the image pickup device 23, a mode setting switch 25 that can issue an instruction relating to the setting of an observation mode of the endoscope system 1, and a storage unit 26 in which endoscope identification information to identify the type or the like of the endoscope 2 is stored in advance.

The image pickup device 23 has, for example, a CMOS imager and is configured to be able to set an exposing period and a reading period of an electric signal for each pixel based on the pixel control signal outputted from the processor 4. In addition, the image pickup device 23 is configured to be driven in response to the image pickup device drive signals outputted from the image pickup device drive unit 24, generate an image based on electric signals read from respective pixels specified by pixel control signals outputted from the processor 4, and output the generated image to the processor 4.

The color filter 23a is formed by disposing a plurality of R (red) filters, G (green) filters, and B (blue) filters each having a predetermined spectral characteristic, respectively, at positions corresponding to respective pixels of the image pickup device 23 in the Bayer pattern (checkerwise).

The R filters of the color filter 23a each have a spectral characteristic that make transmittances in a band between red and near-infrared relatively higher than transmittances in the other bands.

The G filters of the color filter 23a each have a spectral characteristic that make transmittances in a green band relatively higher than transmittances in the other bands.

The B filters of the color filter 23a each have a spectral characteristic that make transmittances in a blue band relatively higher than transmittances in the other bands.

That is, according to the configurations of the image pickup device 23 and the color filter 23a as described above, light passing through the R filters of the color filter 23a, light passing through the G filters of the color filter 23a, and light passing through the B filters of the color filter 23a are received at different pixel groups of the image pickup device 23.

The mode setting switch 25 is configured to be able to issue an instruction to set one of a normal light observation mode and a narrow band light observation mode to the observation mode of the endoscope system 1, in response to an operation by a surgeon or the like.

In the storage unit 26 including a nonvolatile memory or the like, for example, endoscope identification information is stored, the endoscope identification information containing information on the presence/absence of the color filter 23a in the endoscope 2 and information on a pattern of individual filters (R filters, G filters, and B filters) in the color filter 23a. In addition, the storage unit 26 is configured to output the endoscope identification information to the processor 4 when the connection between the endoscope 2 and the processor 4 is detected.

The light source apparatus 3 has an LED light source unit 31, a light source control unit 32 that controls the LED light source unit 31, and a condensing optical system 33 that condenses light emitted from the LED light source unit 31 and supplies the condensed light to the light guide 6.

The LED light source unit 31 has an LED 31r, an LED 31g, and an LED 31b.

The LED 31r is configured to emit NR light, which is red light having a narrow band the central wavelength of which is set at, for example, 610 nm under the control of the light source control unit 32.

The LED 31g is configured to emit NG light, which is green light having a narrow band the central wavelength of which is set at, for example, 540 nm (being an absorption peak of hemoglobin in the blood) under the control of the light source control unit 32.

The LED 31b is configured to emit NB light, which is blue light having a narrow band the central wavelength of which is set at, for example, 415 nm (being an absorption peak of hemoglobin in the blood) under the control of the light source control unit 32.

The light source control unit 32 is configured to be able to cause each LED provided in the LED light source unit 31 to emit and extinguish light, individually, based on light adjustment signals outputted from the processor 4.

The processor 4 has a preprocessing unit 41, an image processing unit 42, a light adjustment unit 43, a pixel control unit 44, and a main control unit 45.

The preprocessing unit 41 is configured to subject an image outputted from the endoscope 2 to processing such as noise removal and output the image subjected to the processing to the image processing unit 42 and the light adjustment unit 43.

The image processing unit 42 subjects the image outputted from the preprocessing unit 41 to image processing such as synchronization to generate a video signal and output the generated video signal to the display device 5, based on a control signal outputted from the main control unit 45.

The light adjustment unit 43 is configured to generate the light adjustment signal based on the control signal outputted from the main control unit 45 and output the generated light adjustment signal to the light source control unit 32.

The pixel control unit 44 is configured to generate a pixel control signal based on the control signal outputted from the main control unit 45 and output the generated pixel control signal to the image pickup device 23.

The main control unit 45, including a CPU, a timing generator, and the like, is configured to output to the image processing unit 42, the light adjustment unit 43, and the pixel control unit 44 a control signal to cause the respective units to perform an operation in accordance with the instruction issued by the mode setting switch 25 and the endoscope identification information outputted from the storage unit 26.

Next, the operations of the endoscope system 1 of the present embodiment will be described. Note that the following description will be made assuming that, among the individual pixels of the image pickup device 23, the pixel group in which the R filters of the color filter 23a are disposed is referred to as an R pixel group, the pixel group in which the G filters of the color filter 23a are disposed is referred to as a G pixel group, and the pixel group in which the B filters of the color filter 23a are disposed is referred to as a B pixel group.

A user such as a surgeon connects the individual units of the endoscope system 1 and further operates the mode setting switch 25 with the power of the individual units of the endoscope system 1 turned on to set the normal light observation mode to the observation mode of the endoscope system 1. In addition, with such operations by the user, the endoscope identification information stored in the storage unit 26 is outputted to the main control unit 45 of the processor 4.

In the meantime, the main control unit 45 identifies the presence/absence of the color filter 23a in the endoscope 2 based on the endoscope identification information outputted from the storage unit 26. Furthermore, when obtaining the result of the identification indicating that the endoscope 2 has the color filter 23a based on the endoscope identification information outputted from the storage unit 26, the main control unit 45 specifies a pixel group that receives light having passed through the R filters, a pixel group that receives light having passed through the G filters, and a pixel group that receives light having passed through the B filters, among the individual pixels of the image pickup device 23.

Then, when obtaining the identification result indicating that the instruction to set the normal light observation mode to the observation mode of the endoscope system 1 has been made with the mode setting switch 25 and the endoscope 2 has the color filter 23a, the main control unit 45 outputs to the light adjustment unit 43 and the pixel control unit 44 a control signal WSYN that causes images of respective R, G, and B color components to be simultaneously acquired at a frame rate FR1.

The light adjustment unit 43 generates, based on the control signal WSYN outputted from the main control unit 45, a light adjustment signal WL that causes the individual LEDs (LEDs 31r, 31g and 31b) of the LED light source unit 31 to simultaneously emit light and simultaneously extinguish the light every period that is set in accordance with the frame rate FR1, and outputs the generated light adjustment signal WL to the light source control unit 32. That is, the provision of such a light adjustment signal WL to the light source control unit 32 causes the NR light, the NG light, and the NB light to be emitted simultaneously from the light source apparatus 3.

The pixel control unit 44 outputs to the image pickup device 23, based on the control signal WSYN outputted from the main control unit 45, a pixel control signal RA that causes all the pixels (the R pixel group, the G pixel group, and the B pixel group) of the image pickup device 23 to be exposed simultaneously every period that is set in accordance with the frame rate FR1, and casuses an image based on electric signals that are read simultaneously from all the pixels of the image pickup device 23 to be generated.

That is, when causing the NR light, the NG light, and the NB light to be emitted simultaneously from the light source apparatus 3, the control based on the control signal WSYN causes control for synchronizing the light-emitting period of the individual LEDs of the LED light source unit 31 (an emitting period of the NR light, the NG light, and the NB light) and the exposing period of all the pixel of the image pickup device 23 in a period PR1 shown in FIG. 2. In addition, when causing the NR light, the NG light, and the NB light to be emitted simultaneously from the light source apparatus 3, the control based on the control signal WSYN causes control for synchronizing the light-extinguishing period of the individual LEDs of the LED light source unit 31 and the reading period of the electric signals from all the pixels of the image pickup device 23 in a period PR2 (different from the period PR1) shown in FIG. 2. FIG. 2 is a diagram illustrating control performed when the normal light observation mode is set to the observation mode of the endoscope system in the embodiment.

In the meantime, the user inserts the insertion portion of the endoscope 2 into the body cavity of an examinee and further operates the mode setting switch 25 with the distal end portion of the insertion portion disposed in proximity to a desired observed site to set the narrow band light observation mode to the observation mode of the endoscope system 1.

When obtaining the identification result indicating that the instruction to set the narrow band light observation mode to the observation mode of the endoscope system 1 has been made with the mode setting switch 25 and the endoscope 2 has the color filter 23a, the main control unit 45 outputs to the light adjustment unit 43 and the pixel control unit 44 a control signal NSEQ that causes images of respective G and B color components to be acquired alternately at a frame rate FR2.

The light adjustment unit 43 generates, based on the control signal NSEQ outputted from the main control unit 45, a light adjustment signal NL that causes the LEDs 31g and 31b to emit (extinguish) light alternately every period that is set in accordance with the frame rate FR2, and outputs the generated light adjustment signal NL to the light source control unit 32. That is, the provision of such a light adjustment signal NL to the light source control unit 32 causes the NG light and the NB light to be emitted alternately from the light source apparatus 3.

The pixel control unit 44 outputs to the image pickup device 23, based on the control signal NSEQ outputted from the main control unit 45, a pixel control signal RB that causes one of the G pixel group and the B pixel group to be exposed every period that is set in accordance with the frame rate FR2, and causes an image based on electric signals that are read from the other pixel group to be generated.

That is, when causing the NG light and the NB light to be emitted alternately from the light source apparatus 3, the control based on the control signal NSEQ causes control for synchronizing the light-emitting period of the LED 31g (the emitting period of the NG light), the exposing period of the G pixel group, the light-extinguishing period of the LED 31b, and the reading period of the electric signals from the B pixel group in a period PR3 shown in FIG. 3. In addition, when causing the NG light and the NB light to be emitted alternately from the light source apparatus 3, the control based on the control signal NSEQ causes control for synchronizing the light-emitting period of the LED 31b (the emitting period of the NB light), the exposing period of the B pixel group, the light-extinguishing period of the LED 31g, and the reading period of the electric signals from the G pixel group in a period PR4 (different from the period PR3) shown in FIG. 3. FIG. 3 is a diagram illustrating control performed when the narrow band light observation mode is set to the observation mode of the endoscope system in the embodiment.

Note that, according to the present embodiment, when the identification result is obtained indicating that the narrow band light observation mode is set to the observation mode of the endoscope system 1 and the endoscope 2 has the color filter 23a, for example, color-shift correction processing may be performed by the image processing unit 42.

As described above, the endoscope system 1 of the present embodiment enables performing control that prevents a period relating to acquiring an image having a G component corresponding to the return light of the NG light and a period relating to acquiring an image having a B component corresponding to the return light of the NB light from overlapping with each other in the case where the narrow band light observation mode is set to the observation mode. As a result, according to the endoscope system 1 of the present embodiment, it is possible to enhance color separation characteristics in the narrow band light observation using the configuration supporting a simultaneous image pickup scheme.

Note that, the endoscope system 1 of the present embodiment may be configured such that, for example, a band limiting filter is inserted into the front face of the LED light source unit 31, the band limiting filter having an optical characteristic that further narrows down the band of the NG light and the band of the NB light in the case where the narrow band light observation mode is set to the observation mode.

In addition, the present embodiment may be configured to cause the NR light supplied from the light source apparatus 3 to the light guide 6 to be generated using only an LED that emits a light beam having a single band, or to be generated using a plurality of LEDs in combination that emit light beams having bands different from one another.

In addition, the present embodiment may be configured to cause the NG light supplied from the light source apparatus 3 to the light guide 6 to be generated using only an LED that emits a light beam having a single band, or to be generated using a plurality of LEDs in combination that emit light beams having bands different from one another.

In addition, the present embodiment may be configured to cause the NB light supplied from the light source apparatus 3 to the light guide 6 to be generated using only an LED that emits a light beam having a single band, or to be generated using a plurality of LEDs in combination that emit light beams having bands different from one another.

On the other hand, the present embodiment may be configured to, for example, when the identification result is obtained indicating that the normal light observation mode is set to the observation mode of the endoscope system 1 and the endoscope 2 has no color filter 23a, perform control supporting a frame-sequential image pickup scheme in which the light-emitting period of the LED 31r (the emitting period of the NR light) is synchronized with the exposing period of the R pixel group in a period PR5, the light-emitting period of the LED 31g (the emitting period of the NG light) is synchronized with the exposing period of the G pixel group in a period PR6 (different from the period PR5), and further the light-emitting period of the LED 31b (the emitting period of the NB light) is synchronized with the exposing period of the B pixel group in a period PR7 (different from both the periods PR5 and PR6).

Note that the present invention is not limited to the above-described embodiment and it should be understood that various alterations and applications are possible without departing the spirit of the invention.

What is claimed is:

1. An endoscope system comprising:
a light source that can emit first narrow band light and second narrow band light different from the first narrow band light sequentially;
a color filter that is formed by disposing at least a first filter and a second filter, the first filter having a spectral characteristic that makes a transmittance in a band of a first color component including a band of the first narrow band light relatively higher than a transmittance in other bands, and the second filter having a spectral characteristic that makes a transmittance in a band of a second color component including a band of the second narrow band light relatively higher than a transmittance in other bands;
an image pickup sensor that is configured to receive light passing through the first filter in a first pixel and receive light passing through the second filter in a second pixel different from the first pixel, and can set an exposing period and a reading period of an electric signal for each pixel; and
a controller that performs control for causing the first narrow band light to be emitted, causing the first pixel to be exposed, and reading an electric signal from the second pixel in a first period, and causing the second narrow band light to be emitted, causing the second pixel to be exposed, and reading an electric signal from the first pixel in a second period different from the first period.

2. The endoscope system according to claim 1, further comprising
a memory in which information on a pattern of the first filter and the second filter in the color filter is stored, wherein
the controller individually specifies the first pixel and the second pixel among respective pixels of the image pickup sensor based on the information stored in the memory.

3. The endoscope system according to claim 1, wherein the controller performs control for synchronizing an emitting period of the first narrow band light, an exposing period of the first pixel, and a reading period of reading an electric signal from the second pixel in the first period, and control for synchronizing an emitting period of the second narrow band light, an exposing period of the second pixel, and a reading period of reading an electric signal from the first pixel in the second period.

4. The endoscope system according to claim 3, wherein light source is further configured to be able to emit the first narrow band light and the second narrow band light simultaneously, and
the controller performs, when causing the first narrow band light and the second narrow band light to be emitted simultaneously from the light source, control for synchronizing the emitting period of the first narrow band light, the exposing period of the first pixel, the emitting period of the second narrow band light, and the exposing period of the second pixel in a third period, and further performs control for synchronizing the reading period of reading the electric signal from the first pixel and the reading period of reading the electric signal from the second pixel in a fourth period different from the third period.

* * * * *